United States Patent [19]
Flock et al.

[11] Patent Number: 5,933,223
[45] Date of Patent: Aug. 3, 1999

[54] OPTICAL DEVICE FOR MEASURING SMALL DIMENSIONS IN VIVO

[75] Inventors: Stephen T. Flock, Little Rock; Scott Ferguson, Vilonia, both of Ark.; Emmanuel B. De Haller, Baar, Switzerland; John L. Dornhoffer, Roland, Ark.

[73] Assignee: Board of Trustees of the University of Arkansas, Little Rock, Ark.

[21] Appl. No.: 08/988,012

[22] Filed: Dec. 10, 1997

Related U.S. Application Data

[60] Provisional application No. 60/032,853, Dec. 13, 1996.

[51] Int. Cl.$^6$ ........................................................ G01C 3/08
[52] U.S. Cl. ........................ 356/4; 356/3; 356/8; 356/18
[58] Field of Search .................................. 356/3, 4, 8, 18

[56] References Cited

U.S. PATENT DOCUMENTS

| | | | |
|---|---|---|---|
| 3,595,220 | 7/1971 | Kawahara | 128/6 |
| 3,817,619 | 6/1974 | Kawahara | 356/1 |
| 3,817,631 | 6/1974 | Kawahara | 356/1 |
| 4,271,829 | 6/1981 | Heckele | 128/6 |
| 5,361,217 | 11/1994 | Makimura et al. | 356/3 |
| 5,699,280 | 12/1997 | Oda et al. | 356/3 |

OTHER PUBLICATIONS

"New Laser Ruler Instrument for Making Measurements Through an Endoscope," Herzon, G.D., *Otolaryngol Head Neck Surg*, pp. 689–692, Jun. 1997.

*Primary Examiner*—Frank G. Font
*Assistant Examiner*—Reginald A. Ratiff
*Attorney, Agent, or Firm*—Ray F. Cox, Jr.

[57] ABSTRACT

A device to measure the relative location in three dimensional space of anatomical structures by injecting a beam of light into an optical imaging device and projecting the beams of light onto the object being imaged. By virtue of the change in the image of the light beam, as a function of changes in the position and/or direction of the injected beam, and knowing the optical transfer function of the imaging device, the position of the anatomical structure can easily be calculated.

20 Claims, 4 Drawing Sheets

OPTICAL DEVICE FOR MEASURING SMALL DIMENSIONS IN VIVO

This application is a continuation of provisional application No. 60/032,853 filed on Dec. 13, 1996.

BACKGROUND OF THE INVENTION

The present invention relates generally to devices that can be used in conjunction with existing optical imaging devices, such as operating room microscopes, for the purpose of measuring small dimensions and in vivo (non-invasively). The present invention relates particularly to a device that exploits the transfer function of an optical imaging device to determine dimensions associated with a source object from the projected image of the source object.

Many surgical procedures are carried out by observation of the surgical field through optical instruments of various types such as operating room microscopes. Both diagnostic and surgical procedures also make extensive use of other optical instruments, such as endoscopes. Such devices provide a magnified image of the patient's anatomical structures. It is desirable to determine the dimensions of anatomical features in the field of the instrument. This is particularly true of procedures carried out in the constricted confines of some surgical fields such as the middle ear. However, such measurements are not easily accomplished.

For example, it is known to use calibrated reticules on an optical instrument to measure lateral dimensions. Changes in the position of the object being imaged with respect to the optical instrument however requires recalibration which is not practical in a surgical setting.

Lateral measurements through an endoscope have been made using twin diode lasers to project parallel beams into the image plane of the endoscope to form two spots in the field of view. Since the distance between the spots is fixed this provides a reference scale in the field of view. Herzon, G. D., et al., "New Laser Ruler Instrument for Making Measurements Through an Endoscope," *Otolaryngology-Head and Neck Surgery*, Vol. 116, p. 689–692 (June 1997).

Devices employing projected parallel light beams to measure the distance to an object are known. For example, U.S. Pat. No. 4,271,829 issued to Heckele discloses a device using two thin parallel visible light rays to measure the distance from the subject to the objective lens of the optical system of an endoscope. Such a device is also disclosed by Kawahara (U.S. Pat. No. 3,817,619; U.S. Pat. No. 3,817,631; and U.S. Pat. No. 3,595,220).

While devices such as graduated reticules are known for making lateral measurements through a surgical optical instrument such as an endoscope or operating room microscope or measurements of the distance of an object from the optical instrument, it is also desirable to measure anatomical structures in three-dimensional space.

SUMMARY OF THE INVENTION

The present invention is an inexpensive means for taking three dimensional measurements of anatomical structures through any optical imaging device. Although the invention is primarily for use through an operating room microscope, such a device can be used though other optical instruments such as an endoscope or standard microscope.

The present invention has no obvious disadvantages. The limitations of the device are dictated by the optical distortions inherent in the optical imaging device with which it is used. Such a limitation can be minimized by using high quality optics.

The present invention makes use of the fact that an object in space with coordinates (x,y,z) can be projected, with an optical device, into an image with coordinates (X,Y,Z). If one knows the transfer function of the optical imaging device, and one knows (X,Y), then one can calculate (x,y).

The same principle may be applied with respect to ray angles between the object and optical device, θ, and the corresponding angle between the optical device and the imaging plane, θ'. Optical fibers and other optics are employed to project a spot on the anatomical feature of interest. By placing a laser on an x,y,(z or θ) stage, and injecting the laser beam into the optical fiber, we can determine X,Y and Z. The output angle is the same as the input angle which is selected by the user and so does not need to be measured. The input angle is defined by positioning the laser on a calibrated mechanical stage.

It is therefore an object of the present invention to provide for a device capable of optically measuring anatomical features imaged through surgical or diagnostic optical instruments.

It is also an object of the present invention to provide for a device capable of measuring small dimensions in vivo.

It is a further object of the present invention to provide for a device for optically measuring objects and anatomical features in three dimensional space.

These and other objects and advantages of the present invention will be seen from a consideration of the following detailed description of the preferred embodiments in conjunction with the drawings which are briefly described as follows:

DETAILED DESCRIPTION OF THE PREFERRED EMBODIMENTS

Generally the present invention is a device to measure the relative location in three dimensional space of anatomical structures by injecting a beam of light into an optical imaging device and projecting the beam of light onto the object being imaged. By virtue of the change in the image of the light beam, as a function of changes in the position, direction and/or focus of the injected beam, and knowing the optical transfer function of the imaging device, the position of the anatomical structure can easily be calculated.

Figure 2:
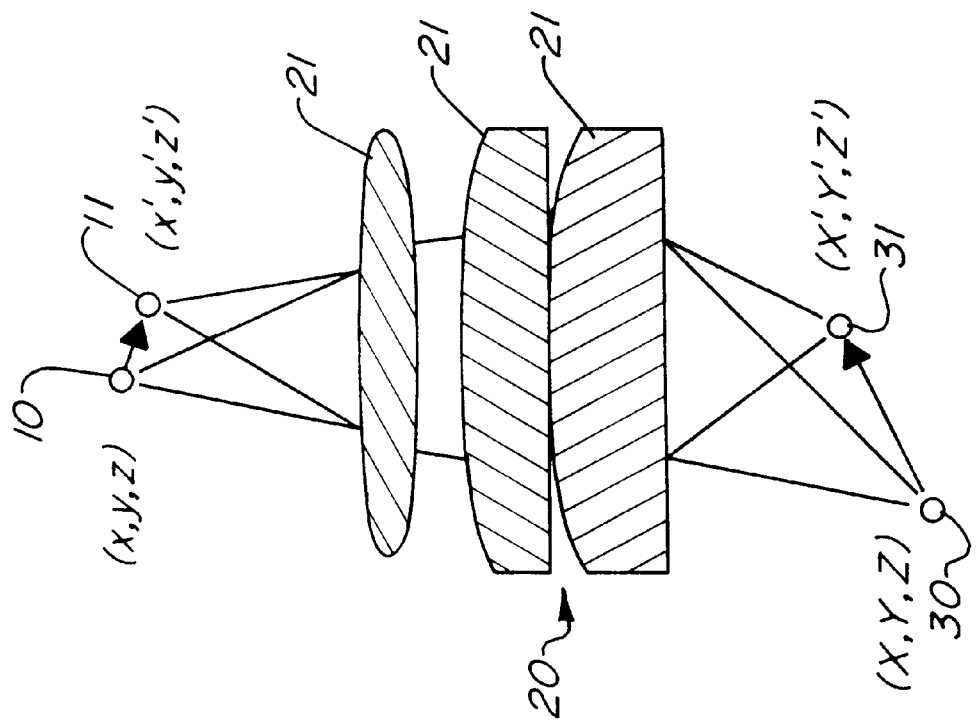
FIG. 2 diagramatically illustrates the effect of moving the source from point (x, y, z) to point (x', y', z') on the projected point which moves from (X, Y, Z) to (X', Y', Z').
Figure 1:
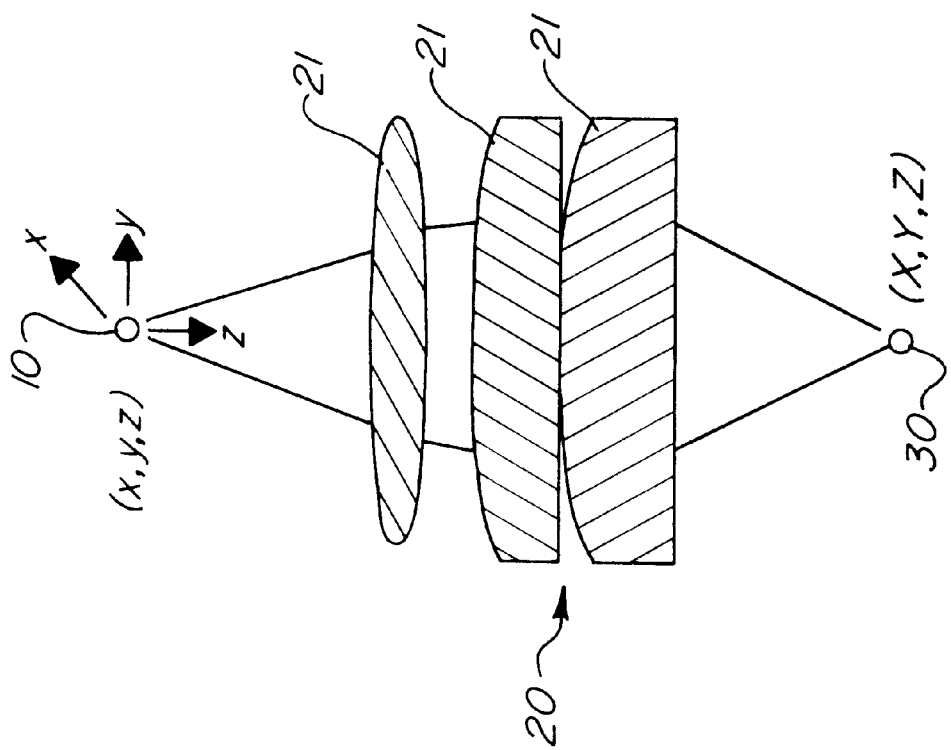
FIG. 1 diagramatically illustrates a source located at (x, y, z) projected by an optical system on a point (X, Y, Z).

Referring to FIGS. 1 and 2, the system uses the basic principle of projection featured by an optical system 20 composed of lenses 21; i.e., the image of a point is projected as a point also. The point may be projected by any means capable of generating a point source of light; however, the preferred source is a laser.

The preferred embodiment of the present invention may be described first with reference to FIG. 1. The present invention makes use of the fact that an object in space may be projected by an optical system 20 to an image located at another location in space and that the relationship between the two locations in space is determined by the transfer function of the optical system 20. FIG. 1 shows, for illustrative purposes only, an optical system 20 of arbitrary configuration consisting of lenses 21. The present invention is not limited to a particular configuration of lenses, but is applicable to any optical system.

A point source 10 or extended shape such as an annulus located in three dimensional space at a point (x, y, z) is projected by the optical system 20 onto a projected point 30, or focused image of the extended shape, at a location in three dimensional space designated arbitrarily as (X, Y, Z). If one knows the transfer function of the optical system 20, and one knows (x,y), then one can calculate (X,Y). The source point 10 may be projected by; e.g., a laser, onto an anatomical feature of interest. It is thus possible to calculate the position in three dimensional space of the projected point 30 which is the position in three dimensional space of the anatomical feature.

If it is desired to know the distance between two anatomical features or the measurement of the length of an extended anatomical feature, the laser beam may be redirected by visual observation as illustrated in FIG. 2 to a second anatomical point 31 located at (X', Y', Z') by moving the laser beam to a second source point 11 located at (x', y', z'). The position of the second anatomical point 31 is calculated by the same procedure, and the distance or measure determined from the two calculated points 30, 31.

The locations (x, y, z) and (x', y', z') of the first source point 10 and second source point 11 are easily determined by mounting the laser beam light source, such as a laser emitting diode or other laser beam source, on a micro x-y-z translation stage. The x-y-z translation stage is desirably operated by a controller, such as a joystick, for x-y translations and a knob for z translations. Each translation is preferably driven by a stepper motor or piezo-crystal driver. The locations of the first source point 10 and the second source point 11 are thus set by the operator.

For the purpose of this description, the coordinate systems for locating points in three dimensional space are arranged so that z and Z are depth coordinates; i.e., z is the depth between the source point 10 and the optical system 20 while Z is the depth between the optical system 20 and the projected point 30. In the embodiment of this device shown in FIG. 1, the depth coordinate, Z, is determined by focusing the laser spot or extended shape such as an annulus to as sharp a focus as possible, and then using the known transfer function of the optical system and the positive lens on the z stage to then allow one to calculate Z. A prototype proving this concept moved a laser on an x,y,z, stage and imaged the spot on a piece of paper some distance away from a simple focusing lens. From known values of (x,y,z), (X,Y,Z) was calculated from a one-time calibration of the optical lens.

In another embodiment, a matrix of spots may be projected to obtain positional information. If the projected matrix is collimated and does not diverge or converge from the source, then, knowing the optical transfer function of the imaging system, it is possible for an operator to simply count the number of spots between two points in the field to get the lateral distance. Alternatively, if the matrix is not collimated, the same information may be obtained by calculation; e.g., by using a microprocessor.

In order to project multiple beams using a single radiant energy source, it is desirable to use an opto-electric device such as an opto-acoustic modulator. Such devices have no moving parts and provide precise control over the deflection of a laser beam transmitted through the device. The device would be located between the source of radiant energy; e.g., a laser, and the object plane.

With reference again to FIGS. 1 and 2, the optical system 20 projects any movement of the source with a proportionality factor f. As the movements $\partial x$, $\partial y$ and $\partial z$ are driven electrically, it is desirable that the simple mathematical operations (analogic) are performed in real time in order to obtain the translation values of $\partial X$, $\partial Y$, and $\partial Z$ of the projected point, i.e. $\partial X = f\, \partial x$, $\partial Y = f\, \partial y$, and $\partial Z = f\, \partial z$. The distance between any two anatomical points of interest is given by the norm of the vector $(\partial X, \partial Y, \partial Z)$. The values of $\partial X$, $\partial Y$, and $\partial Z$ as well as the norm of the vector $(\partial X, \partial Y, \partial Z)$ are desirably displayed in real time. Computers capable of such real time calculation and display function are well known in the art.

Figure 7:
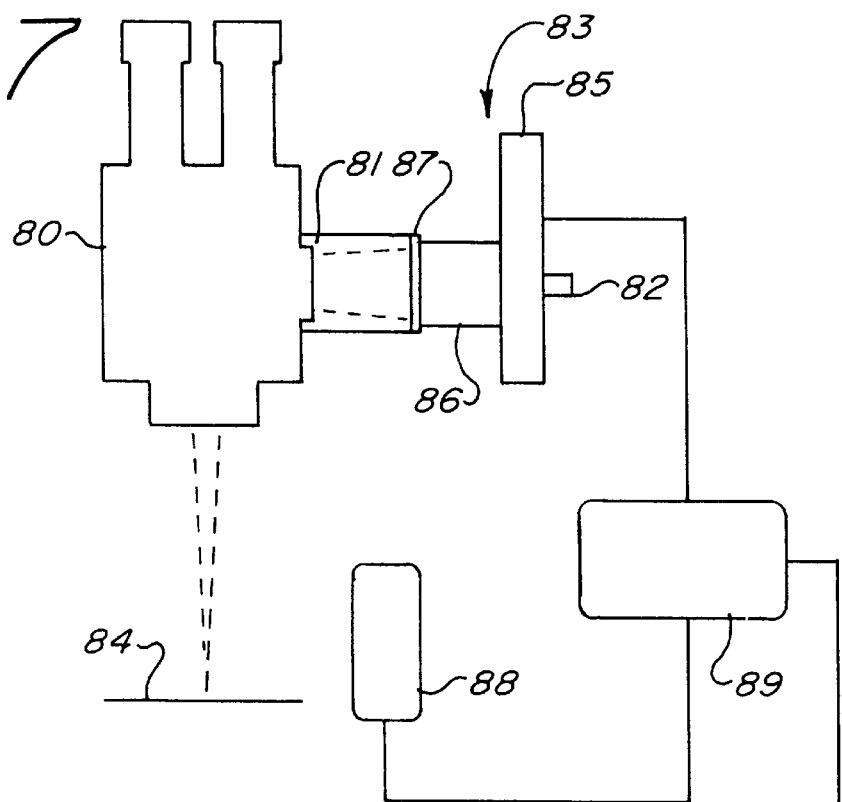
FIG. 7 is a front elevation view of an embodiment of the present invention as used in conjunction with a surgical microscope.

With reference to FIG. 7, the preferred embodiment includes a microscope 80; e.g., a standard binocular surgical microscope. The present invention is not limited however to microscopes or to binocular surgical microscopes. Such microscopes are however easily retrofitted for the practice of the present invention through the use of a standard side port 81. A diode laser 82 is mounted on an x-y-z mechanical stage 83 for projection through the side port 81 and thence through the microscope 80 to the object plane 84. Although other optical sources may be employed in the practice of the present invention, the laser diode is desirable for its compact size, low power consumption, convenience and efficiency. The output of the laser diode 82 should be in the visible light range and its output should be low enough so as not to pose any ocular hazard.

The x-y-z mechanical stage 83 comprises a stepper motor driven x-y stage 85 and a stepper motor driven z stage 86. The stepper motor driven z stage 86 also include a lens 87 so that the focus of the spot projected by the laser diode 82 may be adjusted. Alternatively, the stepper motors may be replaced by servos and encoders. Although less desirable, manually operated micrometers may also be employed. The use of stepper motors or servos and encoders allows for ease of use (the operator need not look up from the microscope) and data representing the position of the x-y-z stage may be fed directly to a microprocessor for automatic calculation of the position of the anatomical structures imaged by the system.

The positioning of the x-y-z stage 83 is therefore accomplished by the operator through a manually operated controller 88 through a driver processor 89 which both drives the x-y stage 85 and the z stage 86 for focusing the spot projected by the laser diode 82. The driver processor may also contain appropriate electronics for deriving data specifying the position of the x-y-z stage 83 and delivering such data to a data processing device 90 to calculate positional information as described herein.

In the preferred embodiment, the operator roughly centers the spot corresponding to the unfocused projection of the source on the object of interest with the x-y stage 85. Then the spot is focused with the z stage 86 to obtain the smallest available spot at the origin of the distance to be measured. The relative origin is reset at (0,0,0). Then the spot is moved toward the end of the distance to be measured, centered and focused as previously described. With the use of a data processing device 90, all the necessary values are displayed in real time.

Figure 3:
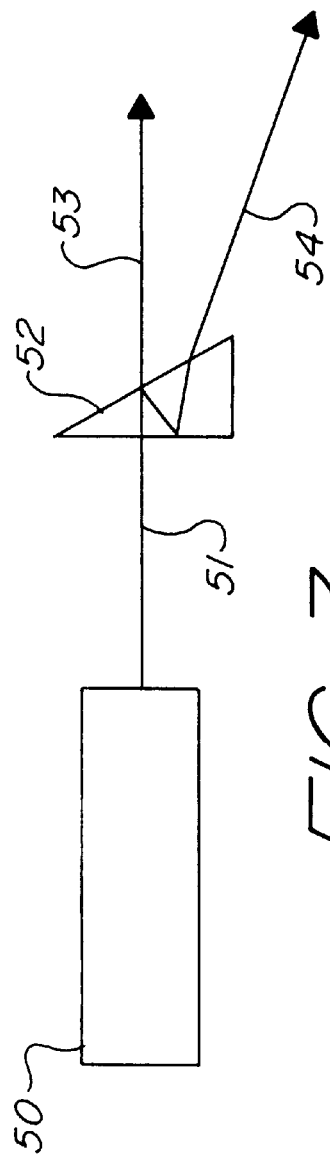
FIG. 3 is a diagramatic illustration of a means for producing two diverging laser beams from a single source beam.
Figure 4:
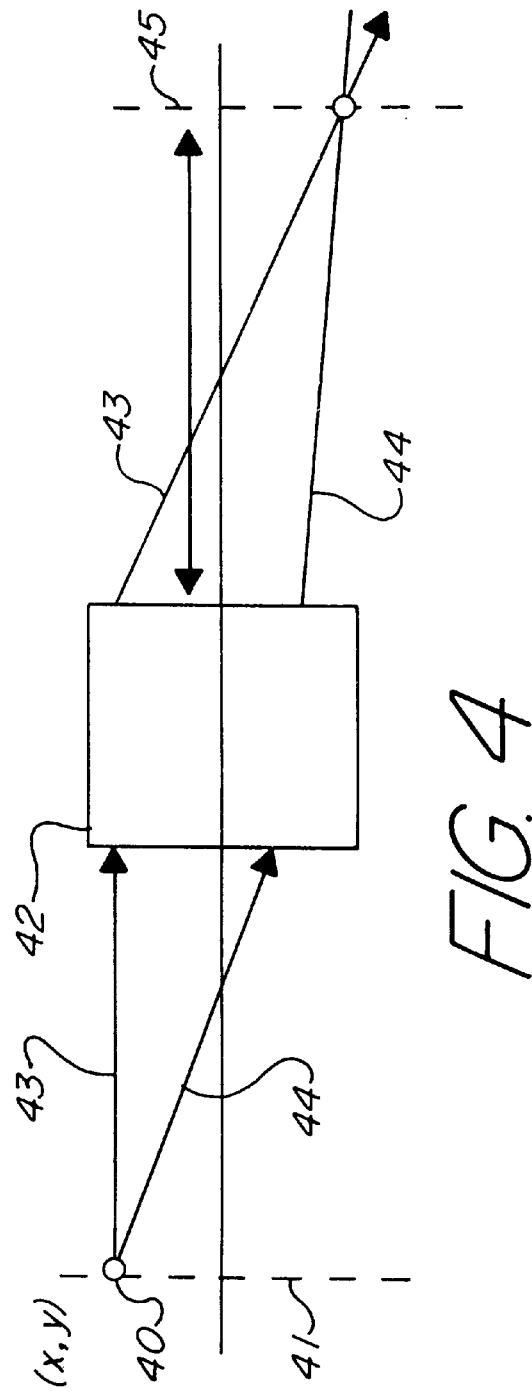
FIG. 4 diagramatically illustrates an embodiment of the present invention employing two diverging laser beams.

An alternative embodiment that would not require a determination by the operator whether the spot is in focus or not, would involve the injection of two laser beams (or one split two ways) into the optical system and adjusting the focus of the device until the two spots meet as one in the image plane. As shown in FIG. 4, a source point 40, designated by coordinates (x, y) is located on the source plane 41. The source plane 41 is the back focal plane of the optical imaging device 42. From the source point 40, two laser beams 43, 44 diverge. Various methods for creating two diverging laser beams are known. One example is shown in FIG. 3, where a laser source 50 generates a laser beam 51. The laser beam 51 is directed to an optical beam splitting device 52; e.g., a prism or diffraction grating, which produces an undeviated beam 53 and a deviated beam 54.

Referring again to FIG. 4, the divergent laser beams 43, 44 are projected through the optical imaging device 42 to the focal plane 45. The two laser beams 43, 44 must be coincident in the focal plane 45 if they start at the same point 40 in the source plane 41. This is true regardless of the angle at which the laser beams impinge on the optical imaging device 42. The distance Z between the optical imaging device 42 and the focal plane 45 can be changed by changing the focus of the optical imaging device 42. The optical imaging device 42 may be calibrated for the distance to the focal plane 45.

Figure 8:
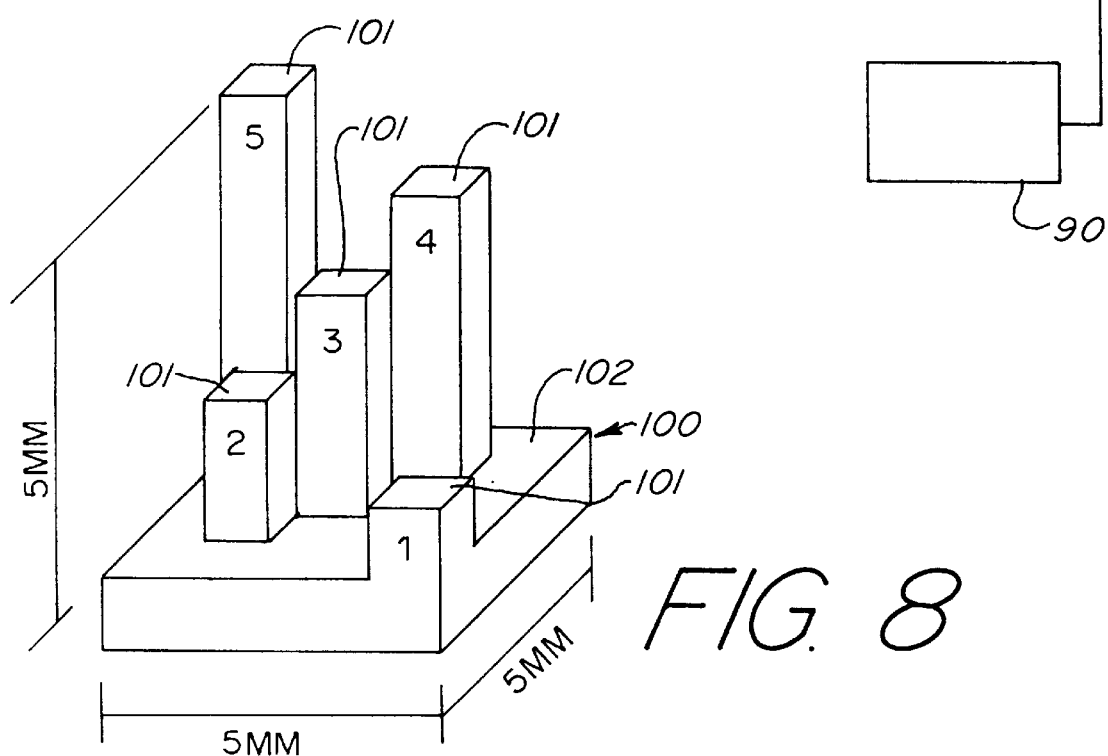
FIG. 8 is a perspective view of a calibration device that may be employed in conjunction with the present invention.

The optical transfer function can be calculated for optical systems, but for complex ones like microscopes, it is easier to determine the optical transfer function by calibration. This technique involves moving the injected laser beam a known amount and measuring the resulting movement in the image plane. The same process may be used for calibrating the focus so that the distance from the optical system to the focal plane may be determined. As shown in FIG. 8, an alternative method of calibration would employ a calibration block 100. The calibration block 100 would be micromachined in order to have a complete three dimensional distribution of surfaces with known distances; e.g., five points scattered in the space within a cube of 5 mm×5 mm×5 mm and a reference of 0 at the surface 102 of the calibration block 100. In the embodiment shown in FIG. 8, calibration points 101 are provided at each 1 mm intervals in each of the x, y, and z axes. Such a calibration device may be particularly desirable if the edges of the optical field are distorted.

An alternative embodiment of the invention employs the same principle as described above with respect to ray angles between the anatomical object of interest and the optical system and the corresponding angle between the optical system and the imaging plane. Optical fibers 60, 61 are employed to project a spot on the anatomical feature of interest 62. It is to be understood that the optical fibers 60, 61 may either incorporate, or be used in conjunction with, focusing optics so that a focused spot is projected by the optical fibers 60, 61. A first laser 63 is placed on a first x,y,(z or θ) stage (not shown), and injects a first laser beam 64 into a first optical fiber 60. A second laser 69 is placed on a second mechanical stage (not shown), and injects a second laser beam 70 into a second optical fiber 61. Adjusting the position of the two lasers 63, 69 to place the spots from the laser beams so as to coincide at the first anatomical point of interest 65, we can determine (X,Y,Z), the location of the first point 65, designated as $P_1$ in the following calculations. The calculations rely on the fact that the output angle from the optical fiber is the same as the input angle which is selected by the user and so does not need to be measured. For example, the input angle 67 to the first optical fiber 60 is the same as the output angle 66, and likewise for the input and output angles associated with the second optical fiber 61. The input angles 67, 70 are defined by positioning the lasers 63, 70 on calibrated mechanical stages.

Figure 5:
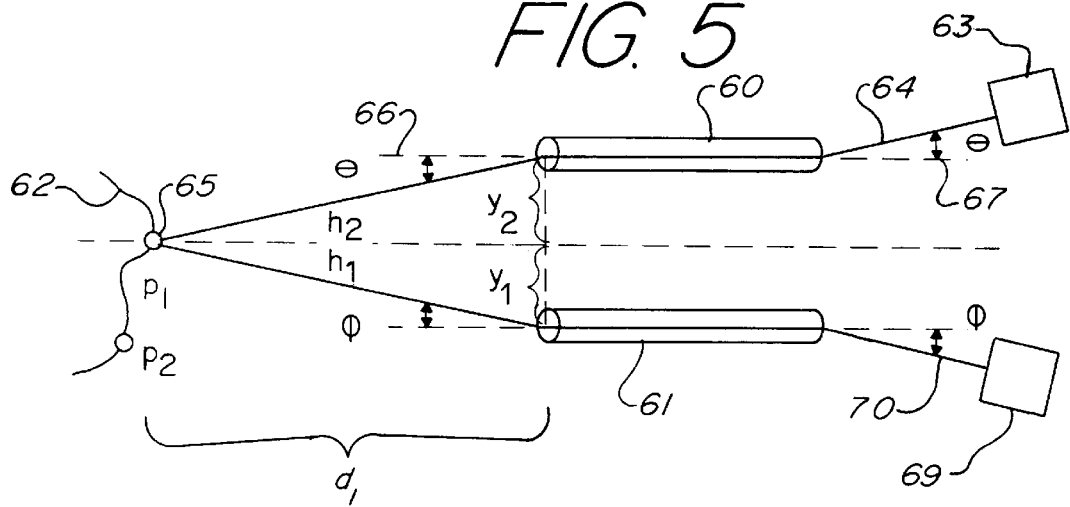
FIG. 5 diagramatically illustrates an embodiment of the present invention which employs a pair of optical fibers to project a spot onto an anatomical feature of interest labeled $p_1$.

Referring to FIG. 5, the laser beam 64 injected into the first optical fiber 60 at input angle 67, designated as θ, comes out of the optical fiber 60 at the same predetermined angle θ, and likewise for the laser beam injected into the second optical fiber at the angle φ. Δy, the distance between the optical fibers 60, 61 is known as is θ and φ.

From the geometry shown in FIG. 5, it is a simple mathematical relationship that $d_1$, the distance along one arbitrary coordinate axis between the point $P_1$ and the output ends of the respective optical fibers 60, 61 is given by either of the two equations:

$$h_2 \tan \theta = d_1 \qquad (\text{Eq. 1})$$

$$h_1 \tan \phi = d_1 \qquad (\text{Eq. 2})$$

Eliminating $d_1$, gives the equation:

$$h_2 \tan \theta = h_1 \tan \phi \qquad (\text{Eq. 3})$$

Likewise, the following relationships are true for the orthogonal distances, $y_1$, $y_2$, from the coordinate axis to the outputs of the respective optical fibers 60, 61:

$$h_2 \sin \theta = y_2 \qquad (\text{Eq. 4})$$

$$h_1 \sin \phi = y_1 \qquad (\text{Eq. 5})$$

We also define:

$$y_2 + y_1 = \Delta y \qquad (\text{Eq. 6})$$

With the four equations, Eqs. 3, 4, 5 and 6, in four unknowns, we can calculate $h_1$, $h_2$, $y_1$, and $y_2$, and thus from Eq. 1 or 2, $d_1$.

Figure 6:
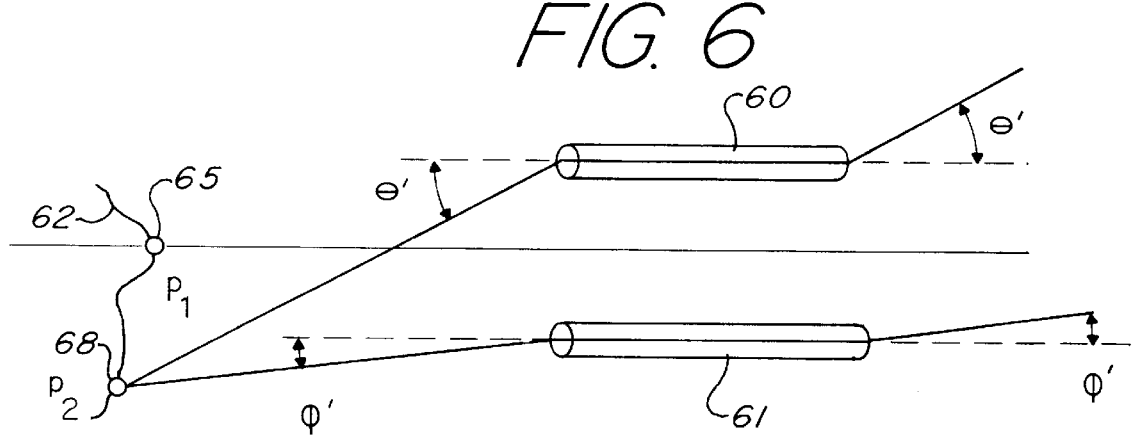
FIG. 6 diagramatically illustrates the embodiment of FIG. 5 showing the change in output angles from one of the optical fiber pair when the input angle from the other of the optical fiber pair is altered to project a spot onto a second anatomical feature of interest, $p_2$ so as to calculate the distance between $p_1$ and $p_2$.

The calculation of a distance between a first point 65 and a second point 68 on the anatomical object of interest 62 is described with reference to FIG. 6. We define the coordinates of first point 65; i.e., $P_1$ (x,y,z) as (0,0,0). The lasers 63, 69 are repositioned on their respective mechanical stages so as to put the spots of the laser beams on the second point 68. The location of the second point 68 is defined as $P_2$. Changing the position of the lasers 63, 69 results in changing the angles into the optical fibers 60, 61 to θ and φ, respectively.

Repeating the calculations described above determines $P_2$ (x,y,z). As described heretofore, the calculation of the distance between first point 65 and second point 68 is a simple vector calculation. Therefore, we can determine distances on an anatomical feature through an endoscope or other optical imaging system. By using a focusing lens in front of the fiber optics, we can use the sharp image of the laser spot to define $d_1$ as described previously, and therefore eliminate some calculations.

An alternative method of determining the length $d_1$ would use an acoustic ultrasonic pressure wave pulse. Simultaneously with the activation of the pressure pulse, a counter circuit would count clock signals until a return is detected by a sound transducer. Once the travel time is known, the distance $d_1$ is calculated by multiplying the velocity of sound by one half of the travel time.

The present invention has been described with reference to certain preferred and alternative embodiments which are intended to be exemplary only and not limiting to the full scope of the present invention as set forth in the appended claims.

What is claimed is:

1. A method of measuring a dimension in three dimensional space of a structure viewed through an optical system characterized by an optical transfer function, comprising the steps of:
   (a) placing a light source at a known first position in three dimensional space;
   (b) projecting a beam of light from the light source into the optical system onto a first point on the structure such that the first point is located in the focal plane of the optical system;
   (c) calculating the position in three dimensional space of the first point from the optical transfer function and the known first position of the light source;
   (d) altering the orientation of the light source to a known second position;
   (e) projecting a beam of light from the reoriented light source into the optical system and focusing the beam of light onto a second point on the structure such that the second point is located in the focal plane of the optical system;
   (f) calculating the position in three dimensional space of the second point from the optical transfer function and the known second position of the light source; and
   (g) calculating the dimension of the structure from the calculated position of the first point on the structure and the calculated second position of the structure as the norm of the vector from the first point to the second point.

2. The method of claim 1 wherein, in steps (b) and (e), the first and second points, respectively, are located in the focal plane of the optical system by focusing the beam of light onto the first and second points, respectively.

3. The method of claim 1 wherein, in steps (b) and (e), the first and second points, respectively, are located in the focal plane of the optical system by injecting a second beam of light into the optical system and adjusting the focus of the optical system to cause the first beam of light and the second beam of light to coincide at the first point and the second point, respectively.

4. A device for measuring a dimension in three dimensional space of a structure viewed through an optical system characterized by an optical transfer function, comprising:
   a light source;
   means for locating said light source at a known first position in three dimensional space;
   means for projecting a beam of light from said light source at said first position into the optical system onto a first point on the structure;
   means for placing said first point into the focal plane of the optical system;
   means for calculating the position in three dimensional space of said first point on the structure from the known first position of said light source and the optical transfer function of the optical system;
   means for locating said light source at a known second position in three dimensional space;
   means for projecting a beam of light from said light source at said second position into the optical system onto a second point on the structure;
   means for placing said second point into the focal plane of the optical system;
   means for calculating the position in three dimensional space of said second point on the structure from the known second position of said light source and the optical transfer function of the optical system;
   means for calculating the dimension of the structure from the calculated position of the first point on the structure and the calculated second position on the structure as the norm of the vector from the first point to the second point.

5. The device of claim 4 wherein said means for locating said light source at a known first position in three dimensional space and said means for locating said light source at a known second position in three dimensional space comprise a mechanical translation stage.

6. The device of claim 5 wherein said means for locating said light source at a known first position in three dimensional space and said means for locating said light source at a known second position in three dimensional space further comprise electro-mechanical means for driving said mechanical translation stage.

7. The device of claim 6 wherein said means for locating said light source at a known first position in three dimensional space space and said means for locating said light source at a known second position in three dimensional space further comprise computing and sensing means for sensing the position of said electro-mechanical translation stage and delivering a data output of said position to said computing means.

8. The device of claim 4 wherein said means for locating said light source at a known first position and said means for locating said light source at a known second position comprise an electro-optic device.

9. A device for measuring a dimension in three dimensional space of a structure, comprising:
   an endoscope for viewing the structure, said endoscope characterized by an optical transfer function;
   a light source for projecting a beam of light into said endoscope and onto a point on the structure;
   means for locating said light source at a known position in three dimensional space;
   means for placing said point into the focal plane of said endoscope; and
   means for calculating the position in three dimensional space of said point on the structure from the known position of said light source and said optical transfer function of said endoscope.

10. The device of claim 9 wherein said means for locating said light source at a known position in three dimensional space comprises a mechanical translation stage.

11. The device of claim 10 wherein said means for locating said light source at a known position in three dimensional space further comprises electro-mechanical means for driving said mechanical translation stage.

12. The device of claim 11 wherein said means for locating said light source at a known position in three dimensional space further comprises computing means and sensing means for sensing the position of said electro-mechanical translation stage and delivering a data output of said position to said computing means.

13. The device of claim 9 wherein said means for locating said light source at a known position comprises an electro-optic device.

14. The device of claim 9 wherein said light source comprises a laser.

15. A device for measuring a dimension in three dimensional space of a structure, comprising:

a microscope for viewing the structure, said microscope characterized by an optical transfer function;

a light source for projecting a beam of light into said microscope and onto a point on the structure;

means for locating said light source at a known position in three dimensional space;

means for placing said point into the focal plane of said microscope; and means for calculating the position in three dimensional space of said point on the structure from the known position of said light source and said optical transfer function of said microscope.

16. The device of claim 15 wherein said means for locating said light source at a known position in three dimensional space comprises a mechanical translation stage.

17. The device of claim 16 wherein said means for locating said light source at a known position in three dimensional space further comprises electro-mechanical means for driving said mechanical translation stage.

18. The device of claim 17 wherein said means for locating said light source at a known position in three dimensional space further comprises computing means and sensing means for sensing the position of said electro-mechanical translation stage and delivering a data output of said position to said computing means.

19. The device of claim 15 wherein said means for locating said light source at a known position comprises an electro-optic device.

20. The device of claim 15 wherein said light source comprises a laser.

\* \* \* \* \*